(12) United States Patent
Biedermann et al.

(10) Patent No.: US 10,092,339 B2
(45) Date of Patent: Oct. 9, 2018

(54) BONE ANCHOR

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 1146 days.

(21) Appl. No.: 13/920,770

(22) Filed: Jun. 18, 2013

(65) Prior Publication Data

US 2014/0012336 A1    Jan. 9, 2014

Related U.S. Application Data

(60) Provisional application No. 61/661,234, filed on Jun. 18, 2012.

(30) Foreign Application Priority Data

Jun. 18, 2012 (EP) ..................................... 12172413

(51) Int. Cl.
*A61B 17/86* (2006.01)
*A61B 17/84* (2006.01)
(Continued)

(52) U.S. Cl.
CPC .......... *A61B 17/844* (2013.01); *A61B 17/864* (2013.01); *A61B 17/866* (2013.01);
(Continued)

(58) Field of Classification Search
CPC . A61B 17/844; A61B 17/861; A61B 17/8615; A61B 17/862; A61B 17/866; A61B 17/8685; A61B 17/864
(Continued)

(56) References Cited

U.S. PATENT DOCUMENTS 7,789,896 B2 * 9/2010 Jackson ............. A61B 17/7032
606/266
8,974,508 B2 * 3/2015 Stephan ............... A61B 17/686
606/304

(Continued)

FOREIGN PATENT DOCUMENTS

CN         1037451 A    11/1989
CN       101530343 A     9/2009
(Continued)

OTHER PUBLICATIONS

Chinese Office action for Application No. 201310232171.2 dated Jan. 25, 2017 and English translation (18 pages).
(Continued)

*Primary Examiner* — Anu Ramana
(74) *Attorney, Agent, or Firm* — Lewis Roca Rothgerber Christie LLP

(57) ABSTRACT

A bone anchor includes an anchor member including a first material, and having a tubular section extending along a longitudinal axis, a region configured to expand radially outwards from the longitudinal axis, and a bone engagement structure projecting from at least a portion of the expandable region of the tubular section, and a core member including a second material, and configured for insertion into and connection to the anchor member. When the core member is in the anchor member and is actuated relative to the anchor member, the tubular section is adjustable between a first position where the expandable region of the tubular member has a first length and a first maximum diameter, to a second position where the expandable region of the tubular member has a length shorter than the first length and a maximum diameter greater than the first maximum diameter.

33 Claims, 8 Drawing Sheets

(51) Int. Cl.
    *A61B 17/70* (2006.01)
    *A61B 17/80* (2006.01)
    *A61B 17/88* (2006.01)

(52) U.S. Cl.
    CPC ...... *A61B 17/8685* (2013.01); *A61B 17/7058* (2013.01); *A61B 17/80* (2013.01); *A61B 17/862* (2013.01); *A61B 17/869* (2013.01); *A61B 17/8615* (2013.01); *A61B 17/8635* (2013.01); *A61B 17/8805* (2013.01)

(58) Field of Classification Search
    USPC .............................. 606/310, 313, 314, 306
    See application file for complete search history.

(56) References Cited

U.S. PATENT DOCUMENTS

| | | |
|---|---|---|
| 2004/0267361 A1 | 12/2004 | Donnelly et al. |
| 2005/0055026 A1 | 3/2005 | Biedermann |
| 2007/0073295 A1 | 3/2007 | Biedermann et al. |
| 2009/0005821 A1 | 1/2009 | Chirico et al. |
| 2009/0131992 A1 | 5/2009 | Greenhalgh et al. |
| 2010/0082071 A1 | 4/2010 | Moumene |
| 2010/0324607 A1 | 12/2010 | Davis |
| 2011/0190830 A1 | 8/2011 | Biedermann et al. |
| 2011/0257689 A1* | 10/2011 | Fiechter ............. A61B 17/8685 606/301 |
| 2011/0319946 A1 | 12/2011 | Levy et al. |
| 2012/0064488 A1 | 3/2012 | Lazarof |
| 2012/0071977 A1 | 3/2012 | Oglaza et al. |
| 2012/0101530 A1 | 4/2012 | Röbling et al. |
| 2014/0288651 A1 | 9/2014 | Biedermann et al. |

FOREIGN PATENT DOCUMENTS

| | | |
|---|---|---|
| CN | 102119870 A | 7/2011 |
| CN | 102427769 A | 4/2012 |
| EP | 2 446 842 A1 | 5/2012 |
| JP | 2005-13740 A | 1/2005 |
| JP | 2006-501908 A | 1/2006 |
| KR | 10 2007 0017016 A | 2/2007 |
| KR | 2007 0017016 A | 2/2007 |
| KR | 10-2010-0108339 A | 10/2010 |
| WO | WO 02/058575 A1 | 8/2002 |
| WO | WO 2009/079329 A2 | 6/2009 |
| WO | WO 2010/105196 A1 | 9/2010 |
| WO | WO 2012/010184 A1 | 1/2012 |

OTHER PUBLICATIONS

Extended European Search Report for European Application No. 12172413.2, European Search Report dated Nov. 6, 2012, and mailed Nov. 15, 2012 (7 pgs).

Search of the Austrian Patent Office by Serv.ip, "Ihr Partner für Forschung und Innovation Express-Recherche zum Stand der Technik," dated Jul. 23, 2012, 5 pp.

* cited by examiner

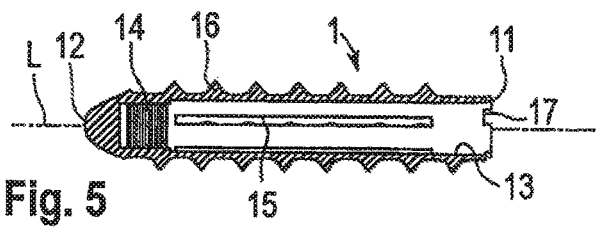
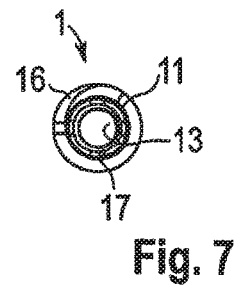
Fig. 5　　　　　　　　　　　　　　　　Fig. 7
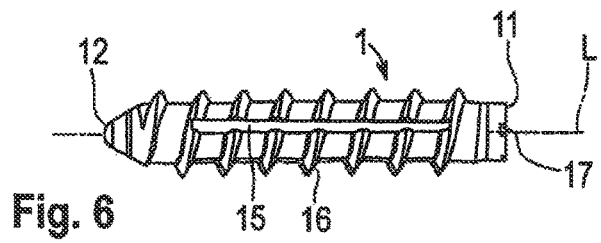
Fig. 6
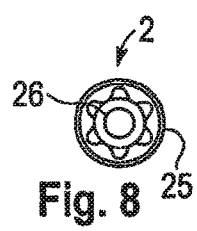　　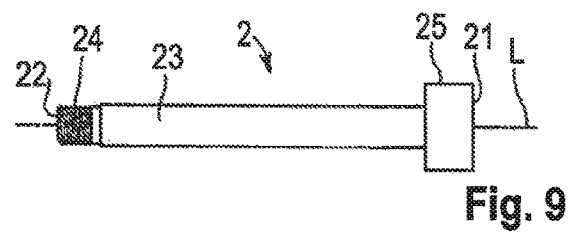
Fig. 8　　　　　　　　　　　　　　　　Fig. 9
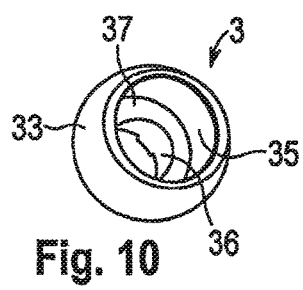　　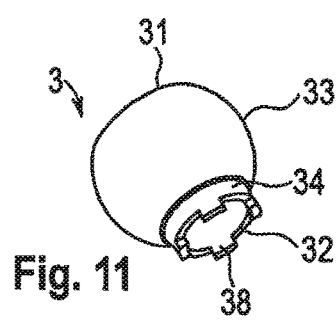
Fig. 10　　　　　　　　　　　　　　　Fig. 11
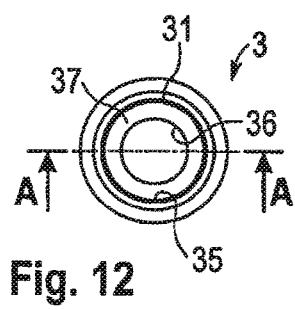　　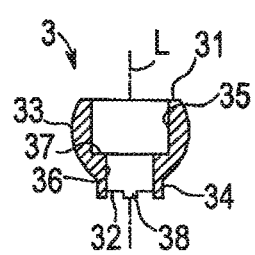
Fig. 12　　　　　　　　　　　　　　　Fig. 13

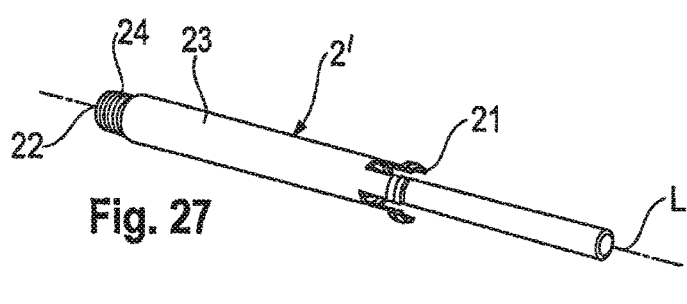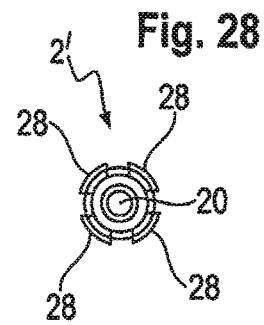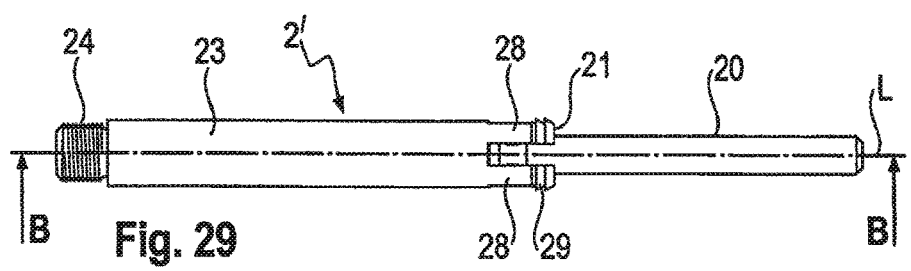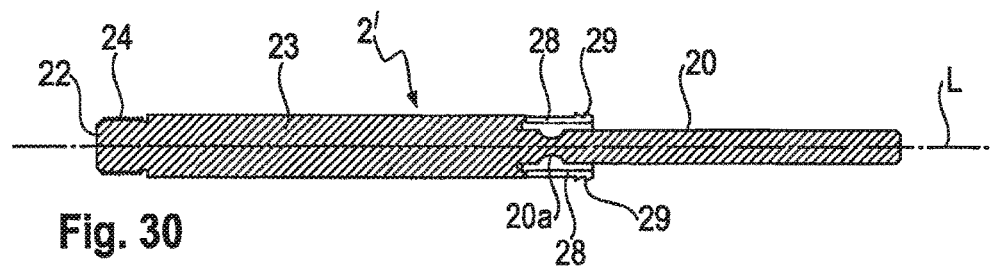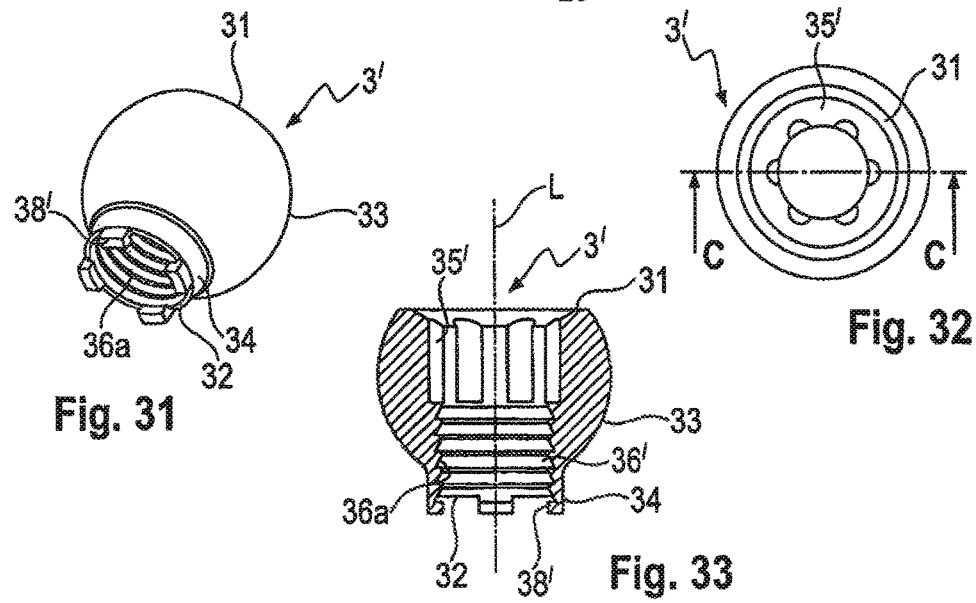

BONE ANCHOR

CROSS-REFERENCE TO RELATED APPLICATION(S)

The present application claims priority to and the benefit of U.S. Provisional Patent Application Ser. No. 61/661,234, filed Jun. 18, 2012, the contents of which are hereby incorporated by reference in their entirety, and claims priority from European Patent Application EP 12 172 413.2, filed Jun. 18, 2012, the contents of which are hereby incorporated by reference in their entirety.

BACKGROUND

Field of the Invention

The invention relates to a bone anchor including an anchor member with an expandable tubular section and a core member insertable into the anchor member and connectable thereto. The core member is configured to cooperate with the anchor member, such that by actuating the core member with respect to the anchor member, the tubular section is expandable. The anchor member is made from a material that is more flexible than a material of the core member. In particular, the bone anchor can be used in a bone fixation or stabilization arrangement, and is especially suitable for anchoring fixation or stabilization devices in osteoporotic bones.

Description of Related Art

US 2009/0131992 A1 describes an attachment device with a radially expandable section. The attachment device can have helical threads to facilitate screwing the attachment device into a bone. The attachment device can be positioned to radially expand the expandable section in cancellous bone substantially surrounded by cortical bone. In particular, the expandable attachment device can have an expandable thread on the expandable section and an unexpandable thread on the unexpandable section. It can be radially expanded by applying a distally-directed force to the distal end.

US 2011/0319946 A1 describes a device for deploying a bone implantation and stabilization assembly into bone tissue, e.g. a spinal structure, vertebrae, cancellous bone, cortical bone etc., in order to stabilize bones and/or bone segments. The bone stabilization device includes an anchor region in the form of an expanding tube or the like including a plurality of anchoring elements or arms that are deployable in a direction away from the axis of the assembly. An actuator is provided for deployment of the anchoring elements.

SUMMARY

As such, there is a need for an improved bone anchor that has a simple design and is easy to manufacture.

It is an object of embodiments of the invention to provide an improved bone anchor that is particularly useful for application in weak bones.

A bone anchor according to embodiments of the invention includes an expandable anchor member and a core member. The anchor member is made of a material that is more flexible than a material of the core member. Hence, the ability of the anchor member to expand in a radial direction results from the material of the anchor member that exhibits a greater flexibility than the material of the core member. This allows for a more simple construction of the anchor member. Preferably, in some embodiments, the material of the anchor member is a polymer material, and the material of the core member is a metallic material.

The expansion of the anchor member can be effected after the anchor member has been inserted into a bone, for example, in situ during surgery.

A separate head may be provided that can be made, preferably, in some embodiments from metallic material. With such a head, the bone anchor can be used with known polyaxial receiving parts and other stabilization devices. Because the head may be a separate part made from a material that is commonly used for stabilization devices, the head can in some embodiments be effectively connected and fixed to such stabilization devices.

The bone anchor according to embodiments of the invention provides for a safe, long term anchoring, in particular in osteoporotic or weak bones.

BRIEF DESCRIPTION OF THE DRAWINGS

Further features and advantages will become apparent from the description of various embodiments by means of the accompanying drawings. In the drawings:

FIG. 5 shows a cross-sectional view in a plane containing a central longitudinal axis of an anchor member of the bone anchor according to the first embodiment;

FIG. 6 shows a side view of the anchor member of FIG. 5;

FIG. 7 shows a top view onto a first end of the anchor member of FIG. 5;

FIG. 8 shows a top view onto a first end of the core member of the bone anchor according to the first embodiment;

FIG. 9 shows a side view of the core member of FIG. 8;

FIG. 10 shows a perspective view from a top onto the head of the bone anchor according to the first embodiment;

FIG. 11 shows a perspective view from a bottom of the head of the bone anchor of FIG. 10;

FIG. 12 shows a top view of the head of FIG. 10;

FIG. 13 shows a cross-sectional view of the head of FIGS. 10 to 12, along line A-A in FIG. 12;

FIG. 27 shows a perspective view of a core member of the bone anchor according to the second embodiment;

FIG. 28 shows a top view from the first end onto the core member of FIG. 27;

FIG. 29 shows a side view of the core member of FIG. 27;

FIG. 30 shows a cross-sectional view of the core member of FIGS. 27 to 29, along line B-B in FIG. 29;

FIG. 31 shows a perspective view from a bottom of a head of the bone anchor according to the second embodiment;

FIG. 32 shows a top view of the head of FIG. 31;

FIG. 33 shows a cross-sectional view of the head of FIGS. 31 and 32, along line C-C in FIG. 32;

FIG. 35b shows an enlarged portion of a detail of FIG. 35a;

DETAILED DESCRIPTION

Figure 1:
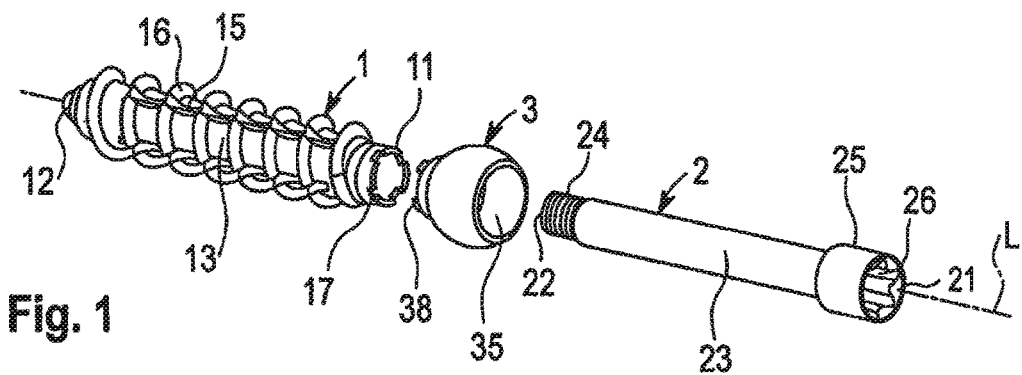
FIG. 1 shows a perspective exploded view of a bone anchor according to a first embodiment.
Figure 2:
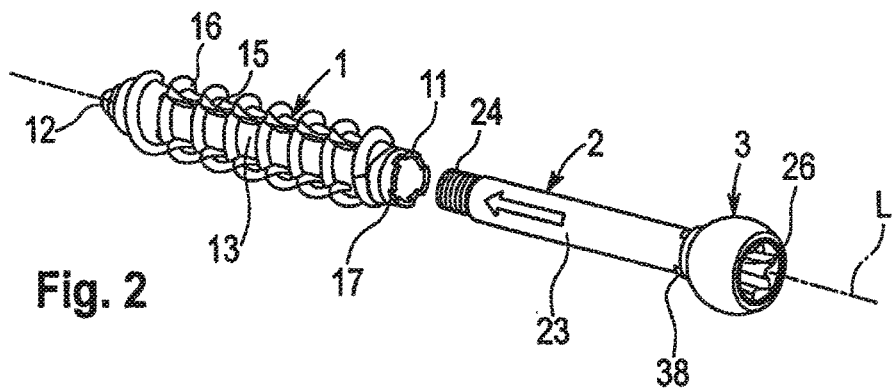
FIG. 2 shows a perspective exploded view of the bone anchor of FIG. 1 with a core member mounted to a head.
Figure 3:
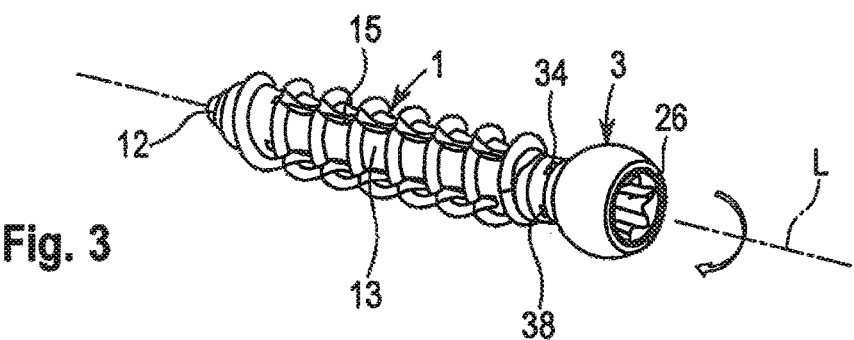
FIG. 3 shows the bone anchor of FIGS. 1 and 2 in an assembled state in a first, non-expanded configuration.
Figure 4:
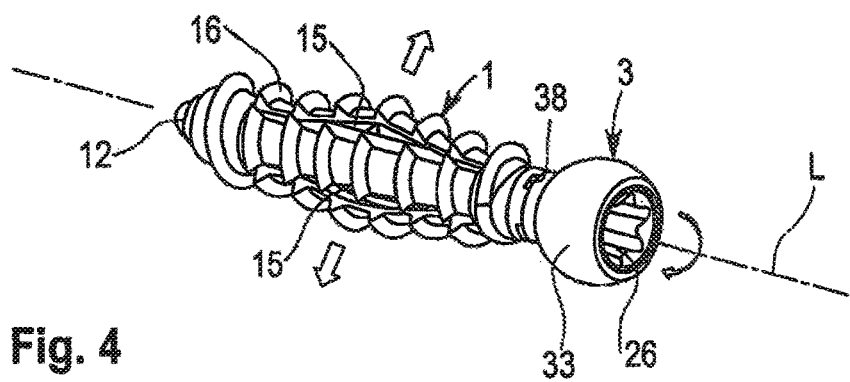
FIG. 4 shows the bone anchor of FIGS. 1 and 2 in an assembled state in a second, expanded configuration.

As shown in FIGS. 1 to 4, a bone anchor according to a first embodiment includes an anchor member 1 in the form of a screw member, a core member 2, and a head 3. The core member 2 can be inserted into the head 3, and an assembly including the core member 2 and the head 3 can be inserted into the anchor member 1 to form the bone anchor. By rotating the core member 2 relative to the anchor member 1, the anchor member 1 can be expanded radially.

As further shown in FIGS. 5 to 7, the anchor member 1 has a first end 11, an opposite second end 12, and a longitudinal axis L extending through the first end 11 and the second end 12. The second end 12 of the anchor member is formed as a tip. Adjacent to the first end 11, there is a tubular section 13 that has a first inner diameter and extends up to a distance from the second end 12. At an end of the tubular section 13 farthest away front the first end 11, a threaded bore 14 is provided with a second inner diameter that is smaller than the first inner diameter of the tubular section 13. In the tubular section 13, at least two, and preferably three or more slits 15 are provided in a wall of the anchor member, where the slits 15 extend in a longitudinal direction substantially parallel to the longitudinal axis L. The slits 15 end at a distance from the first end 11 and at a distance from the second end 12, respectively. By means of the slits 15, the tubular section 13 is rendered flexible, as further described below.

At least a portion of an outer surface of the anchor member 1 is provided with a bone thread 16. Preferably, the bone thread 16 is provided in at least a portion of the tubular section 13 where the slits 15 are located.

At the first end 11, a plurality of recesses 17 extend from a front face of the first end 11 into the tubular section 13, and form engagement portions for a form-fit engagement with the head 3.

The anchor member 1 may be made of a material that has a smaller modulus of elasticity compared to a modulus elasticity of a material of the core member 2. Preferably, the anchor member 1 is made of a polymer material, in particular, a biocompatible polymer material. For example, the material may be selected from among the group of polyaryletherketones (PAEK), including polyetheretherketone (PEEK), polyetherketoneketone (PEKK) and polyetherketone (PEK). However, in various other embodiments, other polymeric materials may also be used. The extent to which the tubular section 13 is expandable can be adjusted during manufacturing by selecting an appropriate material, a wall thickness of the tubular section 13, and a length and width of the slits 15.

It shall be noted that the second end 12 need not to be in the shape of a closed tip. In some embodiments, the second end 12 may be open, and can include teeth at an outer edge. Further, in some embodiments, the inner diameters of the tubular section 13 and of the threaded bore 14 may also be the same.

Furthermore, instead of the bone thread 16, various other bone engagement structures may be provided, such as, for example, barbs or a textured surface.

Figure 16:
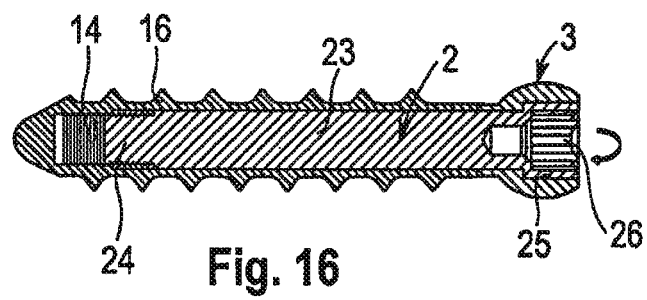
FIG. 16 shows a cross-sectional view of a further step of connecting the core member to the anchor member.

As further shown in FIGS. 8 and 9, the core member 2 has a first end 21, an opposite second end 22, and a rod-shaped central portion 23, the outer diameter of which is only slightly smaller than the inner diameter of the tubular section 13 of the anchor member 1. Adjacent to the second end 22, a portion 24 with an outer thread is provided that cooperates with the threaded bore 14 of the anchor member 1. Adjacent to the first end 21, a cylindrical section 25 with an engagement portion in the form of a recess 26 at the free end forms a drive portion. The engagement portion 26 can have any shape that allows for engagement with a drive tool. For example, the engagement portion 26 can have a hexagon-shape or torx-shape. An outer diameter of the cylindrical portion 25 is greater than the outer diameter of the rod-shaped central portion 23. The length of the rod-shaped central portion 23 is such that, when the core member 2 is assembled with the head 3 and the assembly is inserted into the anchor member 1 as shown in FIG. 16, the threaded portion 24 can engage the thread of the threaded bore 14 of the anchor member 1 at an open end of the threaded bore 14. It should be noted that, instead of a threaded connection between the core member 2 and the anchor member 1, any of various other connections can be used that allows for advancement of the core member into the anchor member, and for holding the core member at a certain position, for example, for withstanding inadvertent sliding back of the core member relative to the anchor member.

The core member 2 is made of a material that is preferably stiffer than the material of the anchor member, for example, a material that has a higher modulus of elasticity. For example, the core member 2 may be made of a metallic material, such as of titanium or stainless steel, or of a body compatible metal alloy, such as, for example, a Ni—Ti alloy, such as Nitinol.

As further shown in FIGS. 10 to 13, the head 3 has a first end 31 and a second end 32. Adjacent to the first end 31, a spherical segment shaped surface portion 33 is provided. A diameter of the head 3 decreases towards the second end 32, and adjacent to the second end 32, a cylindrical neck portion 34 is present. A cylinder axis L corresponds to the longitudinal axis L of the anchor member 1 when the head 3 is connected to the anchor member 1. Adjacent to the first end 31, a first coaxial bore 35 is provided, an inner diameter of which is slightly larger than the outer diameter of the cylindrical portion 25 of the core member 2. Also, a length of the coaxial bore 35 is the same or greater than a length of the cylindrical portion 25 in an axial direction. Adjacent to the cylindrical bore 35, a second cylindrical bore 36 is provided with a diameter smaller than the diameter of the first cylindrical bore 35, but greater than the diameter of the rod-shaped central portion 23 of the core member 2, such that the central portion 23 of the core member 2 may extend therethrough. At a transition between the first cylindrical bore 35 and the second cylindrical bore 36, a shoulder is formed that acts as a support surface 37 for supporting the cylindrical portion 25 in the head 3. Hence, when the core member 2 is inserted into the head 3, the cylindrical portion 25 of the core member 2 rests on the support surface 37.

At the second end 32, a plurality of projections 38 are coaxially arranged at an edge of the second end 32. The projections 38 are shaped and sized so as to allow a form-fit engagement with the recesses 17 of the anchor member 1.

The head 3 is preferably formed of a material that is stiffer than the material of the anchor member 1. In some embodiments, the head 3 is made of the same material as the core member 2, for example, of a metallic material, such as titanium or stainless steel, or of a body compatible metal alloy, such as, for example, a Ni—Ti alloy, such as Nitinol.

The head 3 may facilitate for a connection to other devices, such as receivers of polyaxial anchoring devices or plates, as further described below.

Figure 14:
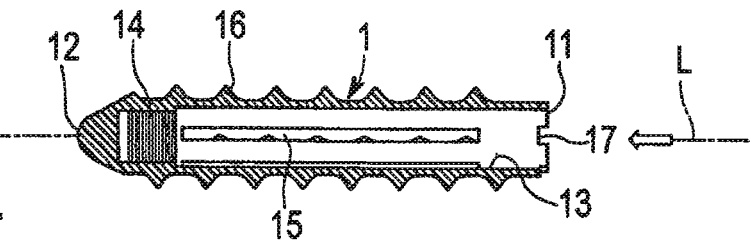
FIG. 14 shows a cross-sectional view of the anchor member of the bone anchor according to the first embodiment in a first step of anchoring the bone anchor in a bone.

A first embodiment of a method of using the bone anchor will be explained with reference to FIGS. 14 to 17. First, as shown in FIG. 14, the anchor member 1 is inserted into a bone, a bone part, or a vertebra (not shown). A core hole may be prepared in the bone in advance. A tool (not shown) may be used that engages the anchor member 1. The engagement portion 17 that serves for a form-fit connection of the anchor member 1 with the head 3 may also be used as an engagement portion for a tool. In some embodiments, other engagement portions (not shown) may instead be provided.

Figure 15:
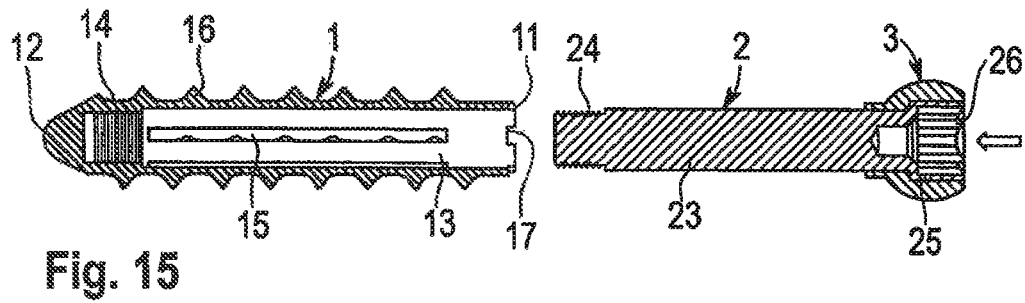
FIG. 15 shows a cross-sectional view of mounting the core member with the head to the anchor member inserted into the bone.

In a second step, as shown in FIG. 15, the preassembled core member 2 and head 3 are inserted into the anchor member 1. Because the core member 2 is supported on the support surface 37 of the head 3, pushing the core member 2 into the tubular section 13 will also move the head 3 towards the anchor member 1. Then, as shown in FIG. 16, the projections 38 of the head 3 engage with the recesses 17 at the first end 11 of the anchor member 1, so that the head 3 and the anchor member 1 are rotationally fixed with respect to each other. In the configuration shown in FIG. 16, the threaded portion 24 just engages the open end of the threaded bore 14. By further rotation of the core member 2, the core member 2 is advanced into the threaded bore 14. Because the core member 2 abuts against the support surface 37 of the head 3, a compressive force is exerted that serves to shorten a distance between the first end 11 and the second end 12 of the anchor member 1. By means of this, the tubular section 13 is radially expanded due to the slits 15, as shown in FIG. 17.

Figure 17:
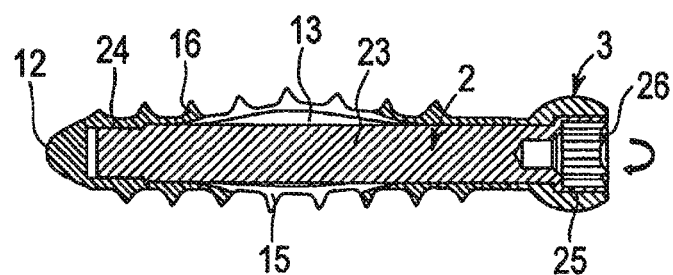
FIG. 17 shows a cross-sectional view of rotating the core member to expand the anchor member.
Figure 18:
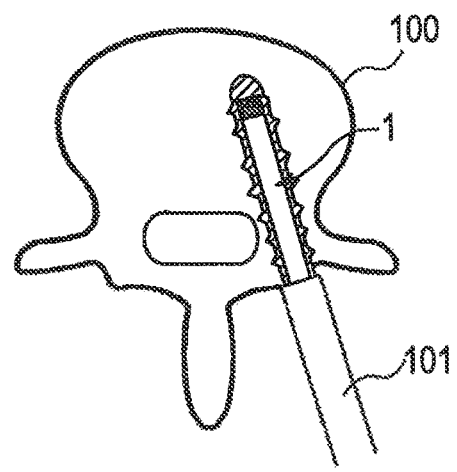
FIGS. 18 to 21 show steps of anchoring the bone anchor in a pedicle of a vertebra according to the first embodiment.
Figure 19:
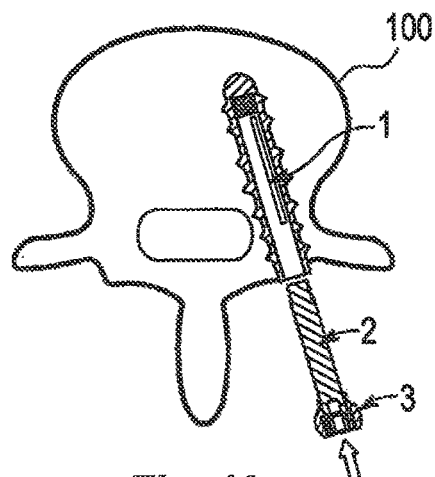
Figure 20:
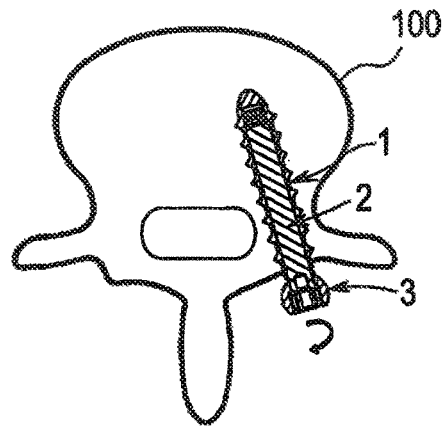
Figure 21:
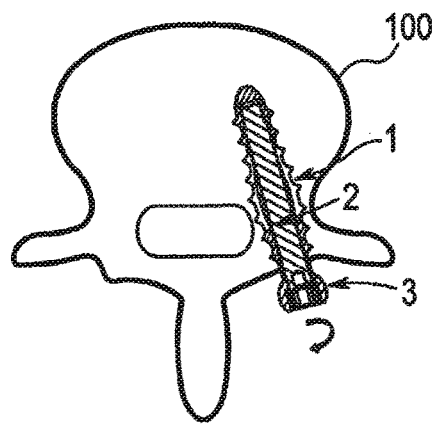

FIGS. 18 to 21 show a method of use, as described above, with an application of the bone anchor to a pedicle of a vertebra 100, corresponding to the steps shown in FIGS. 14 to 17. FIG. 18 depicts the insertion of the anchor member 1 with a tool 101. As shown in particular in FIG. 18, the expansion of the tubular section 13 is effected when the core member 2 has been inserted into the anchor member 1. Especially in weak osteoporotic bone regions, the anchoring strength of the bone anchor can be increased when the anchor member 1 is expanded.

In a second embodiment of a method of use the preassembled anchor member 1 with core member 2 and head 3 as depicted in FIG. 16 are inserted as a whole assembly into an osteoporotic bone, and then the anchor member 1 is expanded as shown in FIG. 17 by rotating the core member 2.

Figure 22:
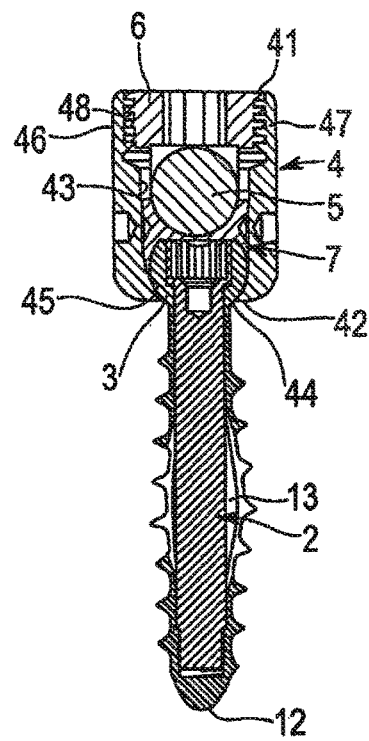
FIG. 22 shows a cross-sectional view of a polyaxial bone anchoring device with the bone anchor according to the first embodiment.

A first application of the bone anchor together with a stabilization device is shown in FIG. 22. The bone anchor according to the first embodiment is received in a receiving part 4 of a polyaxial bone anchor. The receiving part 4 according to one embodiment is substantially cylindrical and has a top end 41, a bottom end 42, and a coaxial bore 43 extending from the top end 41 to a distance from the bottom end 42. The bore 43 narrows towards the bottom end 42 and provides for an opening 44. Near the bottom end 42, a seat 45 is provided for pivotably receiving the head 3. A U-shaped recess extends from the top end 41 to a distance from the bottom end 42 for receiving a rod 5. By means of the U-shaped recess, two free legs 46, 47 are provided which have an internal thread 48 for inserting a locking member 6. Further, a pressure member 7 is provided that exerts pressure onto the head 3, such that the head 3 can be locked in a certain angular position by tightening the locking member 6. In other embodiments, the bone anchor may be used with other parts of receiving parts and designs for polyaxial bone screws. Also, for example, the head 3 of the bone anchor may be designed such that it has a section for receiving a rod and/or for receiving a locking member to fix the rod, as known from, for example, monoaxial bone screws.

Figure 23:
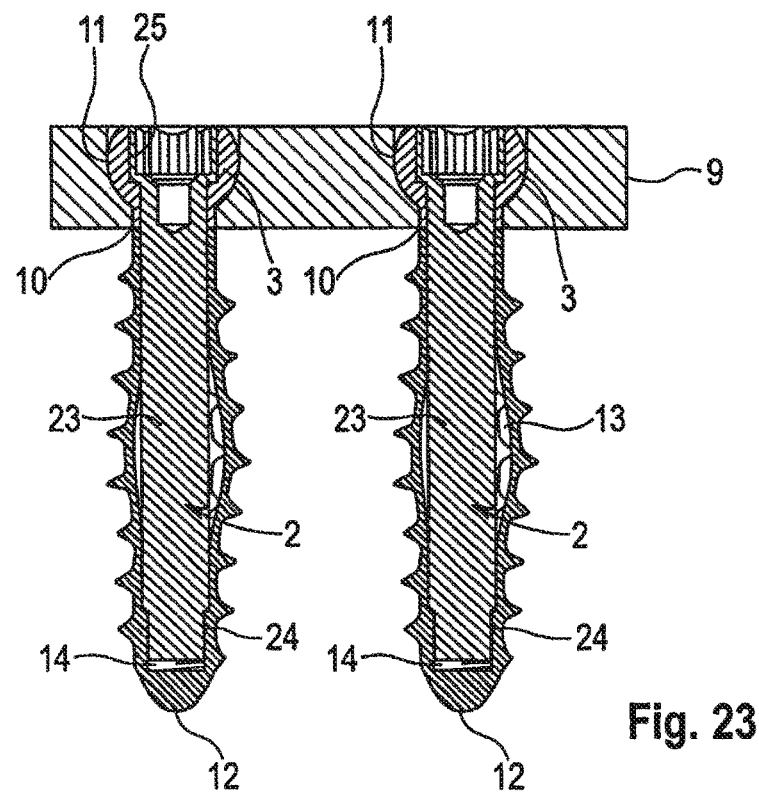
FIG. 23 shows a cross-sectional view of a bone plate with the bone anchor according to the first embodiment.

A second example of an application is shown in FIG. 23, where bone anchors according to the first embodiment are used together with a bone plate 9 that has holes 10 and seat portions 11 for receiving the head 3. Many different configurations of such bone plates are conceivable. Also here, the head 3 may be adapted in its shape to correspond to receiving portions provided in the bone plate.

Figure 24:
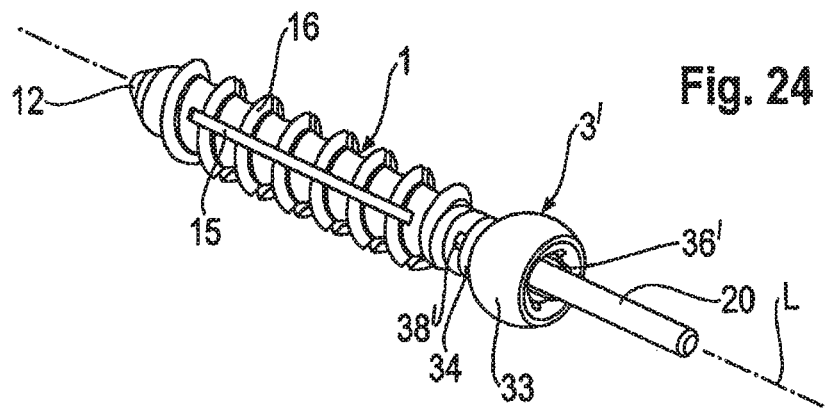
FIG. 24 shows a perspective view of a bone anchor in an assembled state in a first non-expanded configuration according to a second embodiment.
Figure 25:
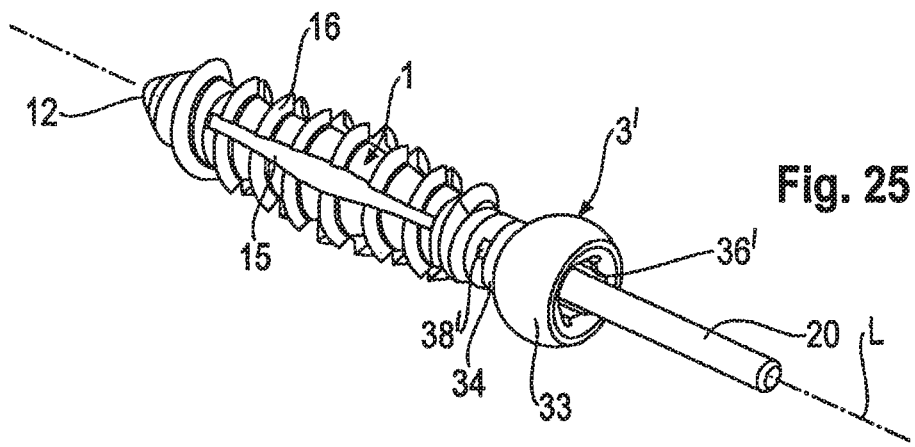
FIG. 25 shows a perspective view of the bone anchor in an expanded configuration according to the second embodiment.
Figure 26:
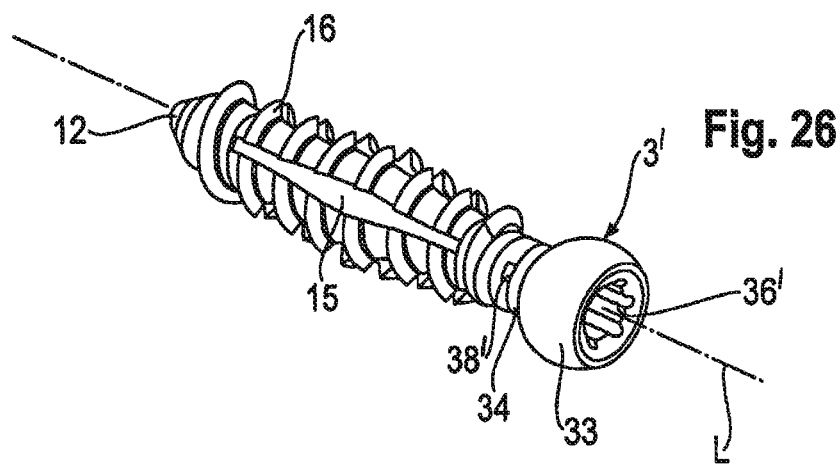
FIG. 26 shows a perspective view of the bone anchor of FIG. 25 in the second, expanded configuration, where a traction member has been broken off.

Referring to FIGS. 24 to 26, a second embodiment of a bone anchor is shown. The anchor member 1 is identical or similar to the anchor member 1 of the first embodiment. The core member 2' acts as a traction element, and may include a traction portion 20. When the core member 2', that has been connected to the anchor member 1 at the second end 12, is pulled using the traction portion 20, a distance between the first end 11 and the second end 12 of the anchor member 1 can be shortened, and the tubular section 13 can be expanded, as shown in FIG. 25. The traction portion 20 may be a break-off portion, and may be broken off after expansion of the tubular section 13, as shown in FIG. 26.

The core member 2' will be described in more detail with reference to FIGS. 27 to 30. The core member 2' includes at its second end 22 an externally threaded portion 24 that cooperates with the threaded bore 14. Further, a rod-shaped central portion 23 is provided. At an end of the central portion 23, a plurality of flexible lips 28 are provided that are arranged around a circumference of an outer surface of the rod-shaped central portion 23 and that extend towards the first end 21. The flexible lips 28 have teeth 29 adjacent to the first end 21 that extend in a circumferential direction and cooperate with corresponding grooves in a head 3', as described further below. The traction portion 20 is a rod-shaped or bar-shaped portion that extends from an end of the central portion 23 between the lips 28 and that projects over or past the first end 21. The traction portion 20 has a break-off portion that is formed as a thinned neck 20a at a position between the lips 28, as shown in FIG. 30. The neck portion 20a has a diameter such that the traction portion 20 may be broken off, for example, by hand or with a tool. A length of the traction portion 20 is such that the traction portion 20 can be gripped and broken off.

Referring further to FIGS. 31 to 33, the head 3' differs from the head 3, in that the head 3' has a first coaxial bore provided with an engagement structure 35' that is located adjacent to a first end 31, and a coaxial bore 36' at a second end 32' that is provided with a groove structure 36a corresponding to the teeth 29 of the core member 2'. Projections 38' at the second end 32 may also have a groove for engagement with the neck 29. All other parts are the same as or similar to the first embodiment.

The teeth 29 and the groove structure 36a of the second bore 36' may have a substantially saw-tooth shape, such that a horizontal flank is oriented towards the second end 32 of the head 3'. The core member 2' and the head 3' cooperate in such a manner that a movement of the core member 2' towards the first end 31 of the head 3' is allowed, whereas a movement in the opposite direction is prevented or restricted due to the engagement of the teeth 29 in the groove structure 36a. It shall be noted that any other engagement structure that fulfils the same or similar function may also be utilized.

Figure 34:
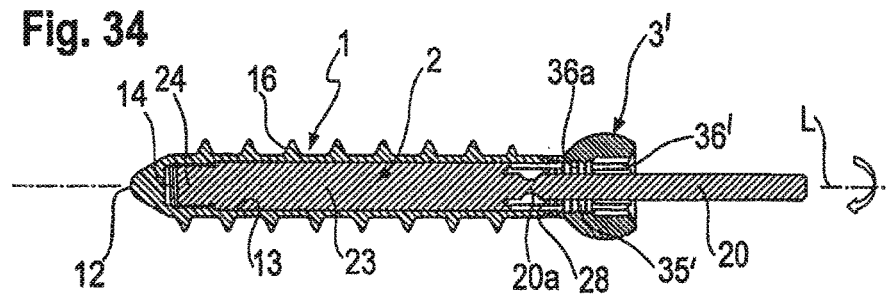
FIG. 34 shows a cross-sectional view of a first step of using the bone anchor according to the second embodiment.

The length of the rod-shaped central portion 23 is such that, when the core member 2' is fully inserted into the anchor member 1, the lips 28 may not yet engage the groove structure 36a of the second bore 36' of the head 3', as shown in FIG. 34.

In use, as shown in FIG. 34, in a first step, the bone anchor is pre-assembled. The core member 2' is inserted into the anchor member 1 until its threaded portion 24 is fully screwed into the threaded bore 14, such that the rod-shaped central portion 23 abuts against a shoulder formed between the threaded hole 14 and the tubular section 13. The head 3' is mounted to the anchor member 1 in a rotationally fixed manner by engagement of the recesses 17 of the anchor member 1 with the projections 38 of the head 3'. The traction portion 20 extends beyond the head 3' out of the rest of the bone anchor, such that the traction portion 20 can be gripped. In this configuration, the bone anchor is screwed into a bone or bone part or vertebra.

Figure 35A:
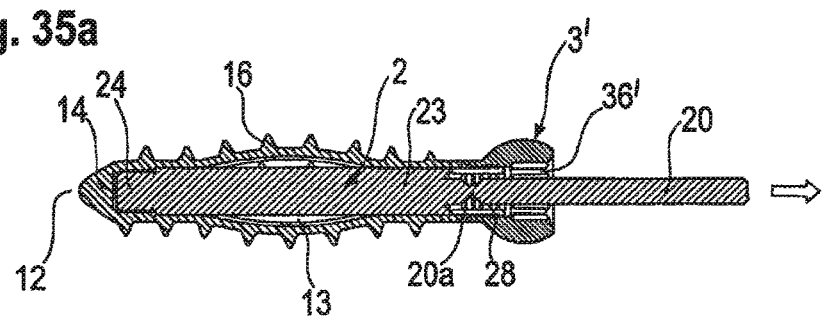
FIG. 35a shows a cross-sectional view of the bone anchor of FIG. 34 in a second, expanded configuration.
Figure 35B:
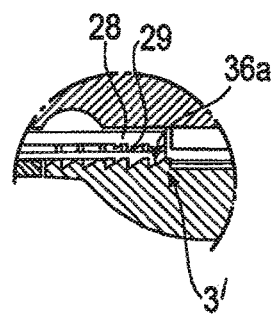

Thereafter, as shown in FIGS. 35a and 35b, the core member 2' is pulled in a direction of the arrow, or in other words, away from the anchor member 1 until the lips 28 with the teeth 29 engage the groove structure 36a of bore 36' of the head 3'. By means of this, because the head 3' is fixed to the anchor member 1, a distance between the first end 11 and the second end 12 of the anchor member 1 can be reduced and the flexible section 13 can be expanded. Such expansion is maintained because the cooperation of the teeth 29 with the groove structure 36a prevents relative movement of the core member 2' in a direction that would enlarge the distance between the first end 11 and the second end 12 of the anchor member 1.

Figure 36:
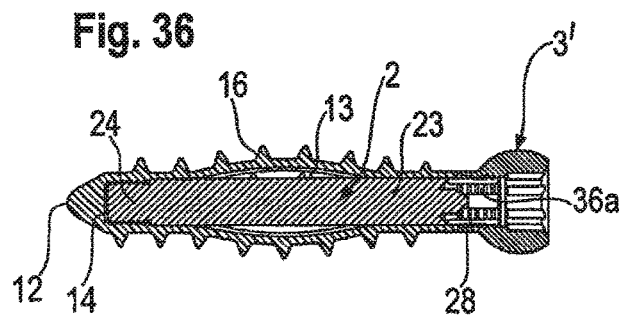
FIG. 36 shows a cross-sectional view of the bone anchor according to the second embodiment, inserted into the bone and expanded, where the traction member has been broken off.

When a desired expansion is achieved, the traction portion 20 can be broken-off at the neck portion 20a, as shown in FIG. 36.

Figure 37:
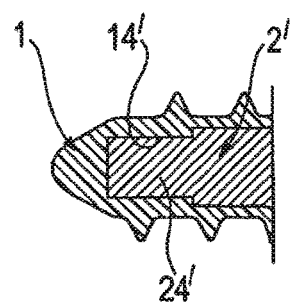
FIGS. 37 to 39 show enlarged cross-sectional partial views of further modifications of a connection between an anchor member and a core member, for example, as seen in the second embodiment.
Figure 38:
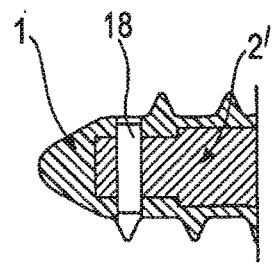
Figure 39:
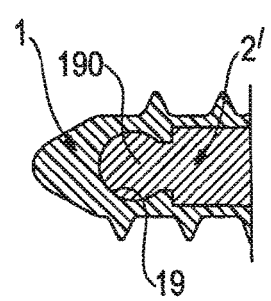

The connection between the core member 2' and the anchor member 1 at the second end 12 need not be a threaded connection. For example, as depicted in FIG. 37, the anchor member 1 may have a threadless bore hole 14' and the core member 2' may have a corresponding threadless portion 24' that can be press-fit into the bore hole 14'. In a further modification, as seen in FIG. 38, a transverse pin 18 can be used to fix the core member 2' and the anchor member 1 relative to each other at the second end 12. In a still further modification, as seen in FIG. 39, a spherical or cylindrical projection 190 at an end of the core member 2' can snap into a correspondingly shaped recess 19 provided inside the anchor member 1. In various other embodiments, any of various other connections may also be possible for fixing the core member 2' and the anchor member 1 relative to each other at the second end 12, so that a tip of the anchor member can be pulled in a direction towards the head.

Various other modifications of the second embodiment are also possible. For example, the core member can be made of two or more parts. For example, the traction portion with the break-off neck portion can be formed as a separate part that is screwed into a corresponding hole of the core member. Also, it may be conceivable that the engagement mechanism between the core member and the head is also formed as a separate part. For example, the teeth portion can instead be made as a separate ring element that is mounted, for example, screwed, onto the core member.

The bone anchor according to the second embodiment may also be used with receiving parts of polyaxial bone anchoring devices, or may also have an adapted head with legs and a channel to receive a rod, for example, in the form of a monoaxial bone screw. The bone anchor according to the second embodiment may also be used with bone plates or various other stabilization devices.

Also in the second embodiment, like in the first embodiment, the tip at the second end of the anchor member may be omitted. Any other bone engagement structure may be provided, such as for example, barbs. Also, the head may have various different shapes, depending on the intended use of the bone anchor. In some embodiments, the materials and combination of materials may be the same as or similar to the first embodiment.

In still further modifications, the bone anchor may be cannulated. In such embodiments, the core member may be cannulated. This may allow for introduction of substances such as bone cement or drugs to surrounding bone regions.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchor comprising:
   an anchor member comprising a first material, the anchor member having a first end, a second end, a tubular section extending along a longitudinal axis between the first end and the second end and having an expandable region configured to expand radially outwards from the longitudinal axis by reducing a distance between the first end and the second end, and a bone engagement structure projecting from at least a portion of the expandable region of the tubular section for facilitating insertion of the anchor member into a bone; and
   a core member having a first end and a second end, and comprising a second material that exhibits less flexibility than the first material, wherein a portion of the core member is configured to be inserted into the first end of the anchor member and advanced past the expandable region for connecting the second end of the core member to the second end of the anchor member;

wherein the core member is configured to cooperate with the anchor member, such that when the core member is in the anchor member and the second end of the core member and the second end of the anchor member remain connected to one another, the core member is configured to be actuated relative to the anchor member to adjust the tubular section from a first position where the expandable region of the tubular section has a first maximum diameter while a first end and a second end of the expandable region are separated by a first distance, to a second position where the expandable region of the tubular section has a maximum diameter greater than the first maximum diameter while the first end and the second end of the expandable region are separated by a distance shorter than the first distance.

2. The bone anchor of claim 1, wherein the first material is a polymeric material.

3. The bone anchor of claim 1, wherein the second material is metallic.

4. The bone anchor of claim 1, wherein the bone engagement structure comprises a bone thread.

5. The bone anchor of claim 1, wherein the tubular section has at least two slits extending substantially parallel to the longitudinal axis.

6. The bone anchor of claim 1, wherein the second end of the anchor member defines a tip.

7. The bone anchor of claim 1, wherein the first end of the anchor member has a further engagement structure.

8. The bone anchor of claim 7, wherein the further engagement structure is defined by at least one recess extending from a face at the first end of the tubular section into the tubular section.

9. The bone anchor of claim 1, wherein the second end of the anchor member comprises a connection portion configured to engage the core member for establishing a connection between the anchor member and the core member, and for restricting sliding movement of the core member relative to the anchor member in a direction opposite to an insertion direction of the core member into the anchor member.

10. The bone anchor of claim 1, wherein the core member is a substantially rod-shaped member, and wherein the second end of the core member comprises a connection portion configured to engage the anchor member for establishing a connection between the anchor member and the core member, and for restricting sliding of the core member relative to the anchor member in a direction opposite to an insertion direction of the core member into the anchor member.

11. The bone anchor of claim 1, further comprising a head that is connectable to and separable from the anchor member and is configured to be arranged at the first end of at least one of the anchor member or the core member.

12. The bone anchor of claim 11, wherein the head has a spherical segment shaped outer surface.

13. The bone anchor of claim 11, wherein the head has a bore and a support surface for rotationally supporting the first end of the core member.

14. The bone anchor of claim 11, wherein the head has a further engagement structure for connecting to the anchor member, such that the head and the anchor member are configured to be rotationally fixed with respect to one another.

15. The bone anchor of claim 11, wherein the head comprises the second material.

16. The bone anchor of claim 11, wherein the first end of the core member comprises a cylindrical section configured to be supported in and to be rotatable in the head.

17. The bone anchor of claim 11, wherein the first end of the core member comprises an engagement portion for engagement with the head, wherein the engagement portion is configured to allow movement of the anchor member in a first direction relative to the core member to reduce the distance between the first end and the second end of the anchor member, while preventing movement of the anchor member in a direction opposite to the first direction relative to the core member.

18. The bone anchor of claim 17, wherein the core member comprises a traction portion for facilitating movement of the anchor member in the first direction relative to the core member.

19. The bone anchor of claim 18, wherein the traction portion is separable from other parts of the core member.

20. The bone anchor of claim 11, wherein the head is between the core member and the anchor member such that when the core member is actuated relative to the anchor member, the core member is configured to apply a compressive force directly onto the head to adjust the distance between the first end and the second end of the expandable region of the anchor member.

21. The bone anchor of claim 11, wherein the head comprises an abutment configured to directly engage the core member.

22. The bone anchor of claim 1, wherein the second end of the anchor member has a threaded bore, and the second end of the core member comprises a threaded portion configured to engage the threaded bore.

23. The bone anchor of claim 1, wherein the second end of the anchor member has a bore, and the second end of the core member comprises a portion configured to be press-fit into the bore.

24. The bone anchor of claim 1, wherein the second end of the anchor member has a bore, and the second end of the core member comprises a portion configured to be snap-fit into the bore.

25. The bone anchor of claim 1, further comprising a pin configured to fix the second end of the anchor member and the second end of the core member relative to one another.

26. The bone anchor of claim 1, further comprising a head that is connectable to and separable from the anchor member, wherein the head comprises a material that exhibits less flexibility than the first material.

27. The bone anchor of claim 1, further comprising a head that is connectable to and separable from the anchor member, wherein when the head is connected to the anchor member, the head and the anchor member are rotationally fixed with respect to one another.

28. A method of attaching a bone anchor to a bone, the bone anchor comprising an anchor member comprising a first material, the anchor member having a first end, a second end, a tubular section extending along a longitudinal axis between the first end and the second end and having an expandable region configured to expand radially outwards from the longitudinal axis by reducing a distance between the first end and the second end, and a bone engagement structure projecting from at least a portion of the expandable region of the tubular section for facilitating insertion of the anchor member into the bone, and a core member having a first end and a second end, and comprising a second material that exhibits less flexibility than the first material, wherein a portion of the core member is configured to be inserted into the first end of the anchor member and advanced past the expandable region for connecting the second end of the core member to the second end of the anchor member, the method comprising:

inserting the anchor member into the bone;

inserting the core member into the first end of the anchor member and advancing the core member past the expandable region to a first position where the second end of the core member and the second end of the anchor member are connected to one another, and where the expandable region of the tubular section has a first maximum diameter while a first end and a second end of the expandable region are separated by a first distance; and actuating the core member relative to the anchor member to move the core member to a second position in the anchor member while the second end of the core member and the second end of the anchor member remain connected to one another, and where the expandable region of the tubular section has a maximum diameter greater than the first maximum diameter while the first end and the second end of the expandable region are separated by a distance shorter than the first distance.

29. The method of claim 28, wherein the actuating of the core member comprises rotating the core member relative to the anchor member.

30. The method of claim 28, wherein the actuating of the core member comprises pulling of the core member relative to the anchor member in a direction opposite to an insertion direction.

31. The method of claim 30, wherein the core member comprises a traction portion for facilitating the pulling of the core member, and wherein the traction portion is separated from the core member after the core member is in the second position.

32. The method of claim 28, wherein the bone anchor further comprises a head for facilitating attachment to a receiving part of an anchoring device, a bone plate, or other stabilization device.

33. A bone anchor comprising:

an anchor member comprising a first material, the anchor member having a first end having an opening, a second end having a connection portion, a tubular section extending along a longitudinal axis between the first end and the second end and having an expandable region positioned axially between the opening and the connection portion, the expandable region configured to expand radially outwards from the longitudinal axis by reducing a distance between the first end and the second end, and a bone engagement structure projecting from at least a portion of the expandable region of the tubular section for facilitating insertion of the anchor member into a bone; and a monolithic core member having a first end and a second end, and comprising a second material that exhibits less flexibility than the first material, wherein the core member is insertable into the opening at the first end of the anchor member, and wherein the core member is connectable to the connection portion at the second end of the anchor member;

wherein the core member is configured to cooperate with the anchor member, such that when the core member is in the anchor member and the second end of the core member and the connection portion of the anchor member remain connected to one another, the core member is configured to be actuated relative to the anchor member to adjust the tubular section from a first position where the expandable region of the tubular section has a first maximum diameter while a first end and a second end of the expandable region are separated by a first distance, to a second position where the expandable region of the tubular section has a maximum diameter greater than the first maximum diameter while the first end and the second end of the expandable region are separated by a distance shorter than the first distance.

* * * * *

UNITED STATES PATENT AND TRADEMARK OFFICE
CERTIFICATE OF CORRECTION

PATENT NO. : 10,092,339 B2
APPLICATION NO. : 13/920770
DATED : October 9, 2018
INVENTOR(S) : Lutz Biedermann et al.

Page 1 of 1

It is certified that error appears in the above-identified patent and that said Letters Patent is hereby corrected as shown below:

In the Specification

Column 3, Line 55          delete "front" and insert -- from --

Signed and Sealed this
Seventeenth Day of September, 2019

Andrei Iancu
*Director of the United States Patent and Trademark Office*